| United States Patent [19] | [11] Patent Number: 4,812,578 |
| Meul | [45] Date of Patent: Mar. 14, 1989 |

[54] SYNTHESIS OF TETRAMIC ACID

[75] Inventor: Thomas Meul, Visp, Switzerland

[73] Assignee: Lonza Ltd., Gampel/Valais, Switzerland

[21] Appl. No.: 187,547

[22] Filed: Apr. 28, 1988

Related U.S. Application Data

[62] Division of Ser. No. 060,338, Jun. 10, 1987.

[30] Foreign Application Priority Data

Jun. 26, 1986 [CH] Switzerland ............... 2566/86

[51] Int. Cl.$^4$ ........................................... C07D 207/36
[52] U.S. Cl. .................................................. 548/544
[58] Field of Search ......................................... 548/544

[56] References Cited

U.S. PATENT DOCUMENTS

| 2,535,010 | 12/1950 | Croxall | 260/484 |
| 2,784,191 | 3/1957 | Fischer et al. | 260/294.7 |
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |

FOREIGN PATENT DOCUMENTS 192255 of 1986 European Pat. Off.
850007 of 1952 Fed. Rep. of Germany.
183756 of 1982 Japan.

OTHER PUBLICATIONS

Koehler, dissertation Bayreuth (1985).
MacKenzie et al., J.O.C.S., 20, No. 12, (1955), pp. 1695 and 1696.
G. Pifferi et al., Il Farmaco, Ed. Sc., (1977), 32, 602–613.
Sidgwick, "The Organic Chemistry of Nitrogen", 3rd Ed., Oxford (1966), p. 637.
Ho et al., "Cleavage of Ester and Ether With Iodotrimethylsilane", Angewandte Chemie, vol. 15, No. 12, (12/76), pp. 774 and 775.
Cram et al., J. Am. Chem. Soc., 1963, 85, pp. 1430–1437.
Chemical Abstracts 105:226341.
Chemical Abstracts vol. 52, 11124g.
Lowe, J. Chem. Soc., Perkin Trans. I, 1973, 2907–2910.

*Primary Examiner*—David B. Springer
*Attorney, Agent, or Firm*—Fisher, Christen & Sabol

[57] ABSTRACT

4-Benzyloxy-3-pyrrolin-2-one is a new valuable intermediate product for the production of tetramic acid. Processes are described for the production of such intermediate as well as the production of tetramic acid.

9 Claims, No Drawings

SYNTHESIS OF TETRAMIC ACID

This is a divisional of application Ser. No. 060,338, filed on June 10, 1987.

BACKGROUND OF THE INVENTION

1. Field of the Invention

The invention relates to the production of tetramic acid.

2. Background

Tetramic acid is a valuable starting product for the production of beta-lactams, which on their part are used for the production of effective antibiotics (G. Lowe, J. Chem. Soc., Perkin Trans. I, 1973, 2907).

So far advantageous processes for producing tetramic acid are not known to the art. Thus, it is known from Lowe, J. Chem. Soc., Perkin Trans. I, 1973, 2909, the process of converting malonic acid monoethyl ester with glycine ethyl ester in the presence of dicyclohexyl-carbodiimide to N-ethoxy-(carbonyl acetyl) glycine ethyl ester, in a further step cyclizing with a base to 2,4-dioxopyrrolidine-3-carboxylic acid methyl ester and finally decarboxylating to tetramic acid. But the basic disadvantage of such process is the necessary, extremely high diluting of the reaction solution in the last step (3.30 g to 2.5 liters means a 0.1 percent solution), which excludes it from being an economical process on a large scale.

BROAD DESCRIPTION OF THE INVENTION

The main object of the invention is to provide a process for producing tetramic acid which does not have the disadvantages of the above-described prior art process.

The main object of the invention is surprisingly attained in a simple way via the new, simply-accessible intermediate 4-benzyloxy-3-pyrrolin-2-one, which has the formula:

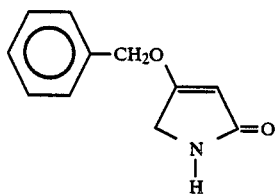

4-benzyloxy-3-pyrrolin-2-one can be prepared by the acid-catalyzed transesterification of 4-alkoxy-3-pyrrolin-2-ones with benzyl alcohol. 4-Alkoxy-3-pyrrolin-2-ones can equally be simply produced from 4-haloacetoacetic acid esters according to the known process of Swiss patent application No. 4119/85. Preferably 4-methoxy-3-pyrrolin-2-one is used as the starting compound.

An anhydrous inorganic acid, for example, sulfuric acid, or a sulfonic acid, for example, methanesulfonic acid, is suitably used as the acid for the transesterification. Methanesulfonic acid is preferably used. The anhydrous inorganic acid (or sulfonic acid) is used in a catalytic amount of suitably 5 to 20 mol percent, preferably 5 to 10 mol percent.

The reactant benzyl alcohol is suitably introduced in an excess of 50 to 200 percent, in relation to the 4-alkoxy-3-pyrrolin-2-one used. Advantageously benzyl alcohol itself functions as a solvent.

The reaction advantageously takes place at a temperature between 60° and 100° C., preferably between 70° and 90° C.

The operation preferably takes place at a reduced pressure, especially between 1 and 50 mbars, to remove from the equilibrium the lower alcohols that have been split off.

After a reaction time of approximately 20 to 30 hours, 4-benzyloxy-3-pyrrolin-2-one can be worked up in a usual way, e.g., by azeotropic evaporation of the excess benzyl alcohol and optionally by subsequent crystallization.

4-Benzyloxy-3-pyrrolin-2-one can be converted into tetramic acid in a simple way by catalytic hydrogenolysis. Palladium, applied to carbon in a suitable amount of from 5 to 20 percent, is an especially suitable catalyst for this purpose.

The operation is advantageously performed in an anhydrous polar aprotic solvent, preferably in tetrahydrofuran, dioxane or dimethylformamide as the solvent. The reaction temperature suitably is between 0° and 40° C. and the reaction pressure is between 1 and 20 bars.

After work-up in a usual way, which depending upon the pressure and temperature can take place after 5 to 10 hours, tetramic acid is obtained in an almost quantitative yield.

Tetramic acid is a valuable starting material for the production of beta-lactams, which on their part are used for the production of effective antibiotics (G. Lowe, J. Chem. Soc., Perkin Trans. I, 1973, 2907).

DETAILED DESCRIPTION OF THE INVENTION

As used herein, all parts, percentages, ratios and proportions are on a weight basis unless otherwise stated herein or otherwise obvious herefrom to one skilled in the art.

THE EXAMPLE

Production of 4-benzyloxy-3-pyrrolin-2-one 5.7 g (50 mmol) of 4-methoxy-3-pyrrolin-2-one and 10.8 g (100 mmol) of benzyl alcohol were mixed with 0.4 g (4 mmol) of methanesulfonic acid and stirred for 24 hours at 80° C. and 20 mbars. Then the reaction solution was mixed with 50 ml of ice water and 100 ml of methylene chloride, and neutralized with 4 ml of saturated $NaHCO_3$ solution. The aqueous phase was extracted twice with 50 ml of methylene chloride each. After drying of the organic phase over $Na_2SO_4$ and distilling off of the solvent, the residue was mixed with 150 ml of ice water, heated to 100° C. and azeotropically distilled off with 100 ml of water-benzyl alcohol. The crystals precipitated during cooling were recrystallized hot from 50 ml of toluene. 6.7 g of white, crystalline product with a melting point of 147° to 148° C. was obtained:

NMR: (300 MHZ, DMSO-$d_6$) in ppm. 7.38 (m, 5H), 6.20 (br. s, 1H), 5.16 (s, 1H), 4.98 (s, 2H), 3.98 (s, 2H).

MS (70 eV): 189 ($M^+$, 40), 172 (18), 132 (51), 91 (100).

Production of 2,4-dioxopyrrolidine (tetramic acid)

1.0 g (5.3 mmol) of 4-benzyloxy-3-pyrrolin-2-one was dissolved in 50 ml of tetrahydrofuran and hydrogenolyzed in the presence of 100 mg of Pd/C (5 percent) for 6 hours at room temperature and 10 bars. Then filtering off from the catalyst was performed and the filtrate was evaporated in a rotary evaporator to dryness. 500 mg of white, crystalline product with a melting point of 120° C. (greater than 120° C. became solid again) was obtained.

NMR: (300 MHz, DMSO-d$_6$) δ in ppm. Enol form: 11.28 (s, 1H), 7.11 (br. s, 1H), 4.76 (s, 1H), 3.74 (s, 2H). Keto form: 8.25 (br. s, 1H), 3.78 (s, 2H), 2.93 (s, 2H).

MS (70 eV): 99 (M+, 32), 71 (78), 43 (58), 42 (100).

What is claimed is:

1. Method for producing tetramic acid of the formula

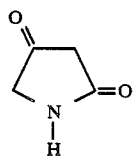

comprising (a) reacting 4-alkoxy-3-pyrrolin-2-one in an acid with benzyl alcohol to provide 4-benzyloxy-3-pyrrolin-2-one of the formula:

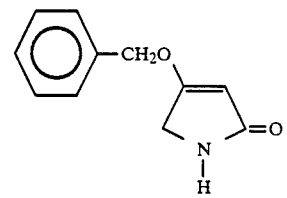

and (b) catalytically hydrogenolyzing the 4-benzyloxy-3-pyrrolin-2-one to provide the tetramic acid.

2. Process according to claim 1 wherein, in step (a), a sulfonic acid or an anhydrous inorganic acid is used as the acid.

3. Process according to claim 2 wherein, in step (a), the reaction is performed at a temperature of 60° to 100° C.

4. Process according to claim 3 wherein, in step (a), the reaction is performed under reduced pressure.

5. Process according to claim 1 wherein, in step (a), the reaction is performed at a temperature of 60° to 100° C.

6. Process according to claim 1 wherein, in step (a), the reaction is performed under reduced pressure.

7. Method according to claim 1, wherein, in step (b), palladium is used as the catalyst.

8. Method according to claim 7 wherein, in step (b), the operation is performed at a temperature of 0° to 40° C. and a pressure of 1 to 20 bars.

9. Method according to claim 1 wherein, in step (b), the operation is performed at a temperature of 0° to 40° C. and a pressure of 1 to 20 bars.

* * * * *